(12) United States Patent
Doppiu et al.

(10) Patent No.: US 8,288,534 B2
(45) Date of Patent: Oct. 16, 2012

(54) PROCESS FOR THE PREPARATION A RUTHENIUM COMPLEX

(75) Inventors: Angelino Doppiu, Seligenstadt (DE); Ralf Karch, Kleinostheim (DE); Kurt Puentener, Basel (CH); Andreas Rivas-Nass, Schries (DE); Michelangelo Scalone, Birsfelden (CH); Roland Winde, Frankfurt (DE); Eileen Woerner, Maintal (DE)

(73) Assignee: Roche Palo Alto LLC, South San Francisco, CA (US)

( * ) Notice: Subject to any disclaimer, the term of this patent is extended or adjusted under 35 U.S.C. 154(b) by 212 days.

(21) Appl. No.: 12/775,415

(22) Filed: May 6, 2010

(65) Prior Publication Data

US 2010/0286403 A1 Nov. 11, 2010

(30) Foreign Application Priority Data

May 7, 2009 (EP) .................................... 09159600

(51) Int. Cl.
C07D 413/14 (2006.01)
C07D 403/02 (2006.01)
C07D 209/48 (2006.01)
C07F 15/00 (2006.01)

(52) U.S. Cl. ..................... 544/139; 548/103; 548/314.7; 548/403; 548/540

(58) Field of Classification Search ................... 544/139; 548/103, 314.7, 403, 540
See application file for complete search history.

(56) References Cited

FOREIGN PATENT DOCUMENTS

WO 2005016944 A1 2/2005
WO 2009124853 A1 10/2009

OTHER PUBLICATIONS

Brady, W. T., et al. "Intramolecular [2+2] Cycloadditions of Ketene Iminium Salts to Carbon-Carbon Double Bonds," Journal of Organic Chemistry, 1987, vol. 52, pp. 2216-2220.

*Primary Examiner* — Rebecca Anderson
(74) *Attorney, Agent, or Firm* — Brian L. Buckwalter

(57) ABSTRACT

The invention relates to a novel process for the preparation of Ruthenium metathesis catalysts of the formula

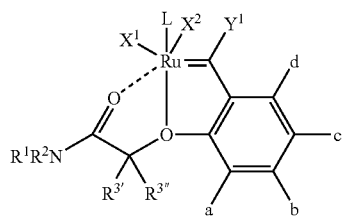

I

Ruthenium metathesis catalysts have been widely applied in the synthesis of macrocyclic drug compounds.

9 Claims, No Drawings

PROCESS FOR THE PREPARATION A RUTHENIUM COMPLEX

CROSS REFERENCE TO PRIOR APPLICATIONS

This application claims the benefit of priority to EP 09159600.7 filed May 7, 2009 the contents of which is hereby incorporated in its entirety by reference.

FIELD OF THE INVENTION

The present invention relates to identification an improved process for the preparation of the hexa-coordinated ruthenium olefin-metathesis complex of formula I which is useful for the manufacture of the HCV protease inhibitor VIII.

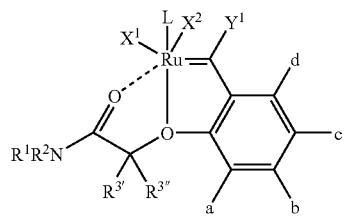
I

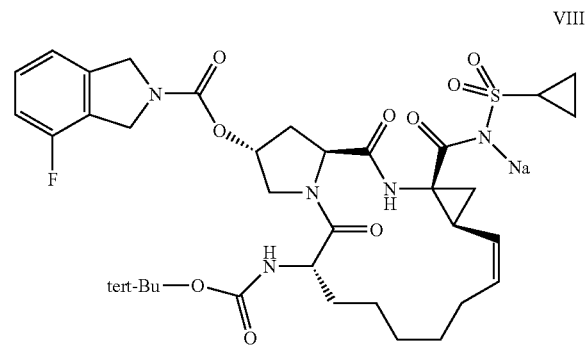
VIII

SUMMARY OF THE INVENTION

The present invention is a process for preparing a ruthenium olefin metathesis catalyst of formula I wherein the dotted line signifies an optional bond; L is a neutral ligand; $X^1$ and $X^2$

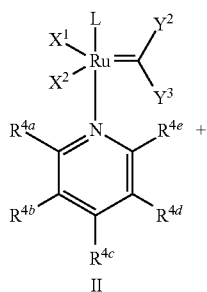
II

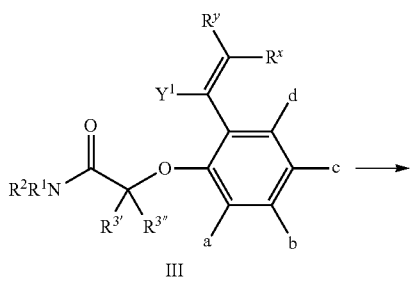
III

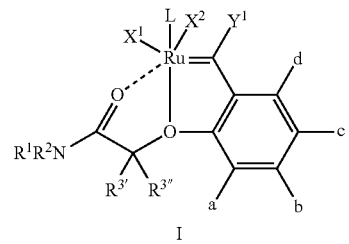
I are independently anionic ligands; $Y^1$ is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl or $C_{1-6}$-alkylsulfinyl; a, b, c and d are independently hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl-or di-$C_{1-6}$-alkylamino, halogen, thio, $C_{1-6}$-alkylthio, arylthio, $C_{1-6}$-alkylsulfonyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$-$C_{1-6}$-alkyl, $OSi(C_{1-6}$-alkyl$)_3$ or $SO_2$-NR'R" wherein R' and R" are independently hydrogen, aryl or $C_{1-6}$-alkyl, or, R' and R" together with the N atom form a cyclic amine; $R^1$ and $R^2$ are independently hydrogen, $C_{1-6}$-alkyl, $C_{3-8}$-cycloalkyl, aryl or aryl-$C_{1-6}$-alkyl, or, $R^1$ and $R^2$ together with the N atom form a 5 to 8 member cyclic amine; and 12$^{3'}$ and $R^{3"}$ are independently hydrogen, $C_{1-6}$-alkyl, $C_{3-8}$-cycloalkyl, aryl or aryl-$C_{1-6}$-alkyl.

The process comprises contacting a ruthenium complex II with a ligand of formula III in an inert organic solvent at temperature from between 0° C. and 100° C. The $X^1$, $X^2$ and L substituents of compound II are as defined in the previous paragraph. $Y^2$ and $Y^3$ are independently hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl; or, $Y^2$ and $Y^3$ taken

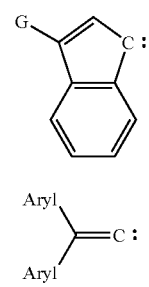
2a

2b

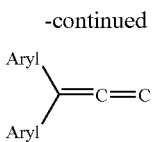

together form a carbene of formula 2a wherein G is hydrogen or aryl, or, $Y^2$ and $Y^3$ together are a vinyl or cumulenyl carbene of formula 2b or 2c; and $R^{4a}$, $R^{4b}$, $R^{4c}$, $R^{4d}$ and $R^{4e}$ are independently hydrogen, $C_{1-6}$-alkyl, $C_{1-6}$-alkyloxy, aryl, aryloxy, halogen, $C_{1-6}$-alkylcarbonyl amino or arylcarbonyl amino.

Suitable ligands for compounds of formula III are $R^1$, $R^2$, $R^{3'}$, $R^{3''}$, $Y^1$, a, b, c and d as defined above; and $R^x$ and $R^y$ are independently hydrogen, $C_{1-6}$-alkyl optionally substituted by one or more halogen atoms, or, aryl optionally substituted by one or more halogen atoms or by $C_{1-6}$-alkyl.

DETAILED DESCRIPTION OF THE INVENTION

Ruthenium metathesis catalysts have been widely applied in the synthesis of macrocyclic drug compounds (see for example the PCT Publication WO 2005/037214 or PCT Publication WO 2007/015824). It is thus important that commercially feasible processes are available for the synthesis of these catalysts. The object of the present invention therefore is to provide a technically feasible manufacturing process for catalysts of general formula I.

The process for the preparation of compounds of formula I comprises contacting a ruthenium complex of formula II wherein $X^1$, $X^2$, L, $Y^2$, $Y^3$, $R^{4a}$, $R^{4b}$, $R^{4c}$, $R^{4d}$ and $R^{4e}$ are as defined hereinabove with a compound of formula III wherein $R^1$, $R^2$, $R^{3'}$, $R^{3''}$, $R^x$, $R^y$, $Y^1$, a, b, c and d are as defined hereinabove and wherein the dotted line signifies an optional bond.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate hydrogen or a substituent or an optional bond as used herein refers either the presence or absence of a bond between the ruthenium atom and an atom of the ligand.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or desired product may not necessarily result directly from the combination of two reagents which were initially added, i.e., there may be one or more intermediates which are produced in the mixture which ultimately leads to the formation of the o and/or the desired product.

The following definitions are set forth to illustrate and define the meaning and scope of the various terms used to describe the invention herein.

The term "$C_{1-6}$-alkyl", alone or in combination with other groups, refers to a branched or straight-chain monovalent saturated aliphatic hydrocarbon radical of one to six carbon atoms, preferably one to four carbon atoms. This term is further exemplified by radicals as methyl, ethyl, n-propyl, isopropyl, n-butyl, s-butyl, t-butyl and pentyl or hexyl and its isomers.

The term "$C_{2-6}$-alkenyl", alone or in combination with other groups, refers to a branched or straight-chain monovalent unsaturated aliphatic hydrocarbon radical of two to six carbon atoms, preferably two to four carbon atoms. This term is further exemplified by radicals as vinyl, propenyl, butenyl, pentenyl and hexenyl and their isomers. Preferred alkenyl radical is vinyl.

The term "$C_{2-6}$-alkynyl", alone or in combination with other groups, refers to a branched or straight-chain monovalent unsaturated aliphatic hydrocarbon radical of two to six carbon atoms, preferably two to four carbon atoms. This term is further exemplified by radicals as ethynyl, propynyl, butynyl, pentynyl or hexynyl their isomers.

The term "$C_{3-8}$-cycloalkyl" group refers to a cycloalkyl group containing from 3 to 8 carbon atoms, such as cyclopropyl, cyclobutyl, cyclopentyl, cyclohexyl, cycloheptyl or cyclooctyl.

The term "halogen-$C_{1-6}$-alkyl" refers to a halogen substituted $C_{1-6}$-alkyl radical wherein halogen has the meaning as above. Preferred "halogen-$C_{1-6}$-alkyl" radicals are the fluorinated $C_{1-6}$-alkyl radicals such as $CF_3$, $CH_2CF_3$, $CH(CF_3)_2$, $CH(CH_3)(CF_3)$ or $C_4F_9$.

The term "$C_{1-6}$-alkoxy" refers to a branched or straight-chain monovalent saturated aliphatic hydrocarbon radical of one to six carbon atoms, preferably 1 to 4 carbon atoms attached to an oxygen atom. Examples of "alkoxy" are methoxy, ethoxy, propoxy, isopropoxy, butoxy, isobutoxy and hexyloxy. Preferred are the alkoxy groups specifically exemplified herein.

The alkyl chain of the alkoxy group can optionally be substituted, particularly mono-, di- or tri-substituted by alkoxy groups as defined above, preferably methoxy, or ethoxy or by aryl groups, preferably phenyl. Preferred substituted alkoxy group is the benzyloxy group.

The term "$C_{1-6}$-alkyl carbonyl" refers to $C_{1-6}$-alkyl substituted carbonyl group, preferably to a $C_{1-4}$-alkycarbonyl group. It includes for example acetyl, propanoyl, butanoyl or pivaloyl. Preferred alkyl carbonyl group is acetyl.

The term "$C_{1-6}$-alkylthio" refers to the group $C_{1-6}$-alkyl-S—, preferably $C_{1-4}$-alkyl-S—, e.g. methylthio or ethylthio. Preferred are the alkylthio groups specifically exemplified herein.

The term "arylthio" refers to a group aryl-S—, preferably to phenylthio.

The term "$C_{1-6}$-alkylsulfonyl" refers to a $C_{1-6}$-alkyl substituted sulfonyl group, preferably to methylsulfonyl.

The term "$C_{1-6}$-alkylsulfinyl" refers to a $C_{1-6}$-alkyl substituted sulfinyl group, preferably to methylsulfinyl.

The term "$SO_2$—aryl" refers to a sulfonyl substituted aryl radical. Preferred $SO_2$-aryl radical is $SO_2$-phenyl.

The term "$SO_2$—NR'R''" refers to a sulfonyl group substituted with an amino group NR'R'' wherein R' and R'' are independently hydrogen or $C_{1-6}$-alkyl, or, R' and R'' together with the N atom form a cyclic amine, e.g. pyrrolidine or pyrrole. In one embodiment, $SO_2$—NR'R'' radical is $SO_2$—$N(CH_3)_2$.

The term "mono- or di-$C_{1-6}$-alkyl-amino" refers to an amino group, which is mono- or disubstituted with $C_{1-6}$-alkyl, preferably $C_{1-4}$-alkyl. A mono-$C_{1-6}$-alkyl-amino group includes for example methylamino or ethylamino. The term "di-$C_{1-6}$-alkyl-amino" includes for example dimethylamino, diethylamino or ethylmethylamino. In one embodiment of the present invention the mono- or di-$C_{1-4}$-alkylamino groups are those specifically exemplified herein. It is hereby understood that the term "di-$C_{1-6}$-alkyl-amino" includes a cyclic amine.

The term "cyclic amine" denotes a saturated carbon ring, containing from 3 to 6 carbon atoms as defined above, and wherein at least one of the carbon atoms is replaced by a heteroatom selected from the group consisting of N, O or S and wherein the N-atom is linked to the phenyl ring, for example, piperidine, piperazine, morpholine, thiomorpholine, di-oxo-thiomorpholine, pyrrolidine, pyrazoline, imidazolidine, azetidine.

The term "aryl", alone or in combination with other groups, relates to a phenyl or naphthyl group, which can optionally be mono-, di-, tri- or multiply-substituted by halogen, hydroxy, CN, halogen-$C_{1-6}$-alkyl, $NO_2$, $NH_2$, NH(alkyl), N(alkyl)$_2$, carboxy, aminocarbonyl, alkyl, alkoxy, alkylcarbonyl, $C_{1-6}$-alkylsulfonyl, $SO_2$-aryl, $SO_3H$, $SO_3$-alkyl, $SO_2$—NR'R'', aryl and/or aryloxy. In one embodiment of the present invention the aryl group is phenyl, however the optimal aryl may differ as indicated hereinafter for certain substituents.

The term "aryloxy" relates to an aryl radical attached to an oxygen atom. The term "aryl" has the meaning as defined above. Preferred aryloxy group is phenyloxy.

The term "arylalkyl" relates to an aryl radical attached to an alkyl group. The term "aryl" has the meaning as defined above. Preferred arylalkyl group is benzyl.

The term "aryl carbonyl" refers to an aryl radical attached to a carbonyl group, whereas the term "aryl carbonyl amino" refers to an aryl carbonyl radical attached to an amino group.

The term "halogen" refers to a fluorine, chlorine, bromine or iodine atom, preferably to a chlorine atom.

In one embodiment the starting material for the process of the present invention is a Ru complex of formula II wherein $X^1$, $X^2$, $Y^2$, $Y^3$, $R^{4a}$, $R^{4b}$, $R^{4c}$, $R^{4d}$, $R^{4e}$ and L are as defined herein above.

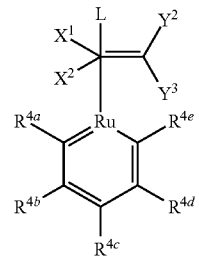

II

In another embodiment the ligand L in formula II is selected from 2q, 2r, 2s or 2t wherein $R^7$ and $R^8$

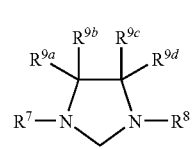

2q

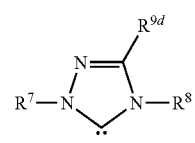

2r

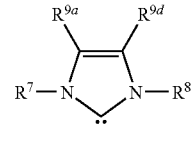

2s

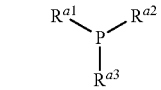

2t independently of each other are $C_{1-6}$-alkyl, aryl, $C_{2-6}$-alkenyl or 1-adamantyl.

$R^{9a-d}$ are independently hydrogen, $C_{1-6}$-alkyl, $C_{2-6}$-alkenyl or aryl; or, $R^{9b}$ and $R^{9e}$, or $R^{9a}$ and $R^{9d}$ taken together are $(CH_2)_4$, or $R^{9a}$ and $R^{9d}$ in formula 2s are both halogen, preferably chlorine.

$R^{a1}$, $R^{a2}$ and $R^{a3}$ independently of each other are $C_{1-6}$-alkyl, $C_{3-8}$-cycloalkyl, aryl or heteroaryl, or, $R^{a1}$ and $R^{a2}$, or, $R^{a2}$ and $R^{a3}$, or $R^{a1}$ and $R^{a3}$ taken together form a 1,5-bridged cyclooctyl group.

In a one embodiment $R^7$ and $R^8$ are $C_{1-6}$-alkyl, 1-adamantyl, a phenyl group which is di- or tri-substituted with $C_{1-6}$-alkyl or a naphthalene which is di- or tri-substituted with $C_{1-6}$-alkyl.

In an embodiment $R^7$ and $R^8$ are t-butyl, 1-adamantyl, isopropyl, 2,6-diisopropylphenyl, 2,7-diisopropylnaphthyl or 2,4,6-trimethylphenyl. In another embodiment $R^7$ and $R^8$ are 2,4,6-trimethylphenyl or 2,7-diisopropylnaphthyl.

In an embodiment $R^{9a}$ and $R^{9c}$ are methyl or phenyl and $R^{9b}$ and $R^{9d}$ are hydrogen, or, $R^{9a}$ and $R^{9c}$ or $R^{9b}$ and $R^{9d}$ are taken together to form a —$(CH_2)_n$— bridge wherein n is 5 or 6. It is hereby understood that if chiral carbon atoms are present, both the racemic and the enantiomerically pure form are encompassed in the present invention.

In another embodiment $R^{9a-d}$ are hydrogen.

In another embodiment $R^{a1}$, $R^{a2}$ and $R^{a3}$ are independently $C_{1-6}$-alkyl, $C_{3-8}$-cycloalkyl or phenyl.

In still another embodiment $R^{a1}$, $R^{a2}$ and $R^{a3}$ are independently cyclohexyl, cyclopentyl, isopropyl or phenyl.

In another embodiment L in formula 2t is $Cy_3P$, $iPr_3P$, $Cyp_3P$ or $Ph_3P$ wherein Cy stands for cyclohexyl, Cyp for cyclopentyl and iPr for isopropyl.

In another embodiment L is 2u and 2v wherein $R^7$ and $R^8$ are as described above.

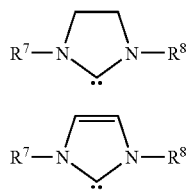

2u

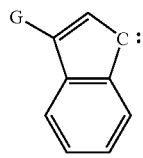

2v

In an embodiment the anionic ligands $X^1$ and $X^2$ are a halogenide or a pseudo halogenide such as cyanide, a rhodanide, a cyanate, an isocyanate, acetate or trifluoroacetate. In another embodiment $X^1$ and $X^2$ are halogenides. In yet another embodiment $X^1$ and $X^2$ are chloro.

In one embodiment $Y^2$ and $Y^3$ are taken together to form a carbene of formula 2a wherein G is hydrogen or aryl. In one embodiment $Y^2$ and $Y^3$ are phenyl.

2a

In another embodiment $R^{4a}$, $R^{4b}$, $R^{4c}$, $R^{4d}$ and $R^{4e}$ are independently hydrogen, $C_{1-6}$-alkyl or halogen. In another embodiment $R^{4a}$, $R^{4b}$, $R^{4c}$, $R^{4d}$ and $R^{4e}$ are independently hydrogen and methyl. In another embodiment $R^{4a}$, $R^{4b}$, $R^{4c}$, $R^{4d}$ and $R^{4e}$ are hydrogen.

The compounds of formula II can be prepared in accord with the disclosure of D. Burtscher, C. Lexer, K. Mereiter, R. Winde, R. Karch, C. Slugovc, *Journal of Polymer Sciences, Part A: Polymer Chemistry*, 2008, 46, 4630-4635).

In another embodiment the compound of formula II is IIa which is commercially available as Neolyst M31 from Umicore AG $ Co. KG, Rodenbacher Chaussee 4, 63457 Hanau-Wolfgang, Germany.

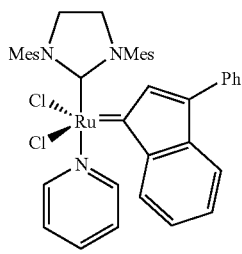

IIa

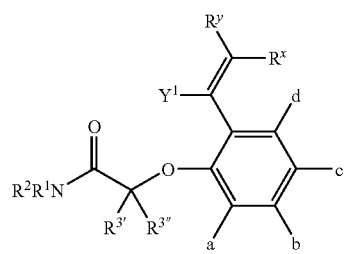

III

The compounds of the formula III wherein $R^1$, $R^2$, $R^{3'}$, $R^{3''}$, $Y^1$, a, b, c and d are as defined herein above and wherein $R^x$ and $R^y$ are independently hydrogen, $C_{1-6}$-alkyl optionally substituted by one or more halogen atoms or aryl optionally substituted by one or more halogen atoms or by $C_{1-6}$-alkyl can be prepared as depicted in scheme 1.

SCHEME 1

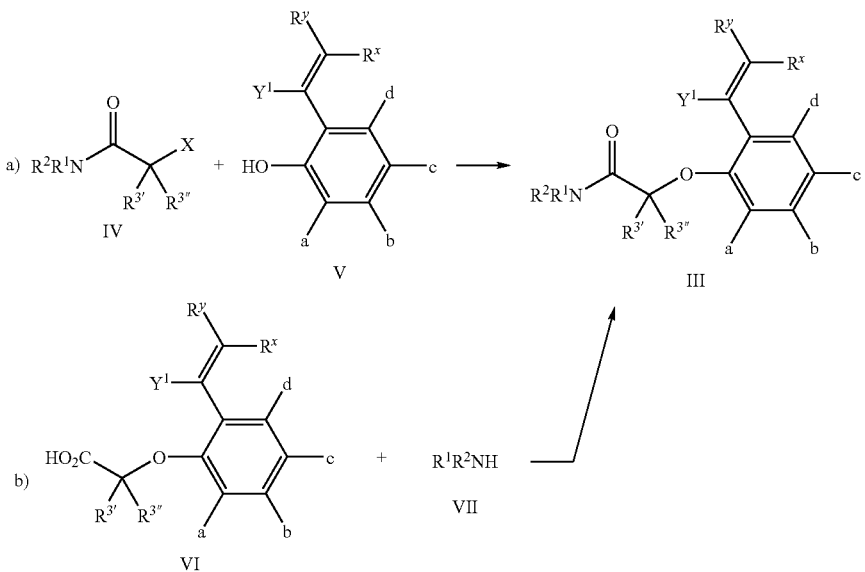

According to the pathway a) of scheme 1, the compounds of formula III can be prepared by standard methods of the organic synthesis, e.g. by treatment of the V with a 2-halo amide IV in DMF with potassium carbonate and cesium carbonate as bases (as reported in M. Bieniek et al., *Journal of Organometallic Chemistry* 2006, 691:5289) or in the presence of sodium hydroxide and a phase transfer agent (as reported in M. Halpern et al., *Synthesis* 1979 177).

Alternatively, according to the pathway b) of scheme 1, compounds of formula III can be prepared by coupling of VI with an amine in the presence of a substituted tetramethyluronium salt such as TBTU (2-(1H-benzotriazol-1-yl)-1,1,3,3,-tetramethyluronium tetrafluoroborate) (G. R. Pettit et al., *J. Nat. Prod.* 1999 62:409) or HBTU (O-(1-benzotriazolyl)-N,N,N',N'-tetramethyluronium hexafluorophosphate (A. Speicher et al., *J. Prakt. Chem.* 1998 340:581).

In one embodiment of the present invention II is treated with a compound according to formula III wherein $Y^1$, a, b and d are hydrogen; c is hydrogen, halogen, nitro, $C_{1-6}$-alkylcarbonyl amino, aryl carbonyl amino, aryl sulfonyl amino, alkyl sulfonyl amino, halogen-$C_{1-6}$-alkyl sulfonyl amino, $SO_2$—NR'R" wherein R' and R" are independently hydrogen, $C_{1-6}$-alkyl, aryl, or R' and R" together with the N atom form a cyclic amine; $R^1$ and $R^2$ are independently hydrogen, $C_{1-6}$-alkyl, or $R^1$ and $R^2$ together with the N atom form a 6 member cycle which contains oxygen as additional hetero atom; R3' and R3" are independently hydrogen or $C_{1-6}$-alkyl; and, $R^x$ and $R^y$ are independently hydrogen or $C_{1-6}$-alkyl.

In another embodiment of the present invention II is treated with a compound according to formula III wherein $Y^1$, a, b and d are hydrogen, c is hydrogen, Cl, nitro or $SO_2$—NR'R"; $R^1$ and $R^2$ are independently hydrogen or $C_{1-6}$-alkyl; $R^{3'}$, $R^{3''}$, $R^x$ and $R^y$ are independently hydrogen or methyl.

In another embodiment of the present invention II is treated with a compound according to formula III wherein the compound of said formula III is IIIa, IIIb, IIIc, IIId, IIIe, IIIf, IIIg or IIIh.

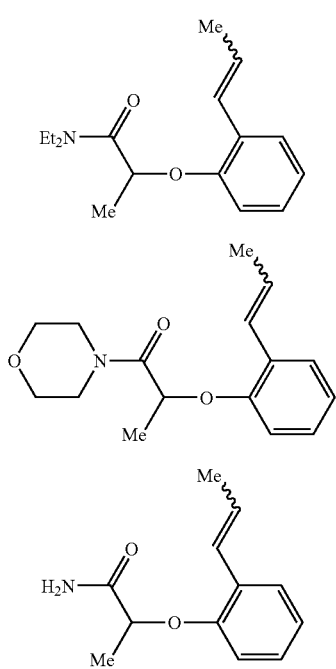

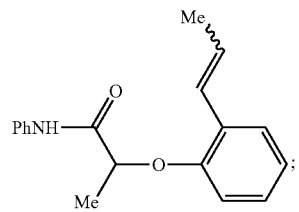

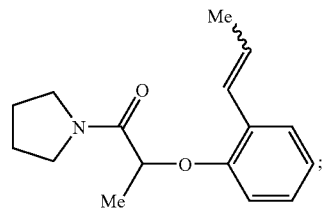

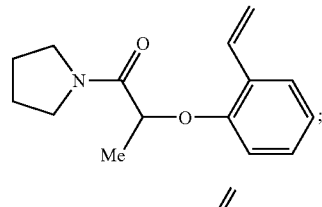

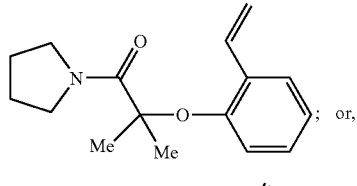

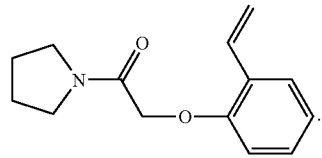

In another embodiment of the present invention II is treated with a compound according to formula III wherein the compound of said formula III is IIIe or IIIf.

In an embodiment of the present invention the conversion is performed in an inert organic solvent such as in an aromatic solvent, a halogenated aromatic solvent, a halogenated hydrocarbon and mixtures thereof or in a mixture of said solvents with an aliphatic hydrocarbon. Suitable aromatic organic solvents are benzene, toluene or mesitylene and suitable halogenated aromatic solvents are polyfluorinated benzenes or toluenes. Useful halogenated hydrocarbons are for example dichloromethane or dichloroethane. Suitable aliphatic hydrocarbon co-solvents can be selected from pentane, hexane or heptane. The solvents may be used as single solvent or as a mixture of different solvents.

In another embodiment of the present invention the inert organic solvent is toluene.

In one embodiment of the present invention the reaction is carried out at 0° C. to 100° C. under an inert gas atmosphere. In another embodiment of the present invention the reaction is carried out at 40° C. to 80° C. under inert gas atmosphere.

The desired compound of formula I can be isolated from the reaction mixture applying methods known to the skilled in the art, usually by filtering off the product and by washing the precipitate with a suitable organic solvent such as with toluene, hexane, pentane and diethyl ether or with mixtures thereof.

The following compounds of formula I are representative of ruthenium metathesis complex catalysts which can be prepared in accordance with the present invention.

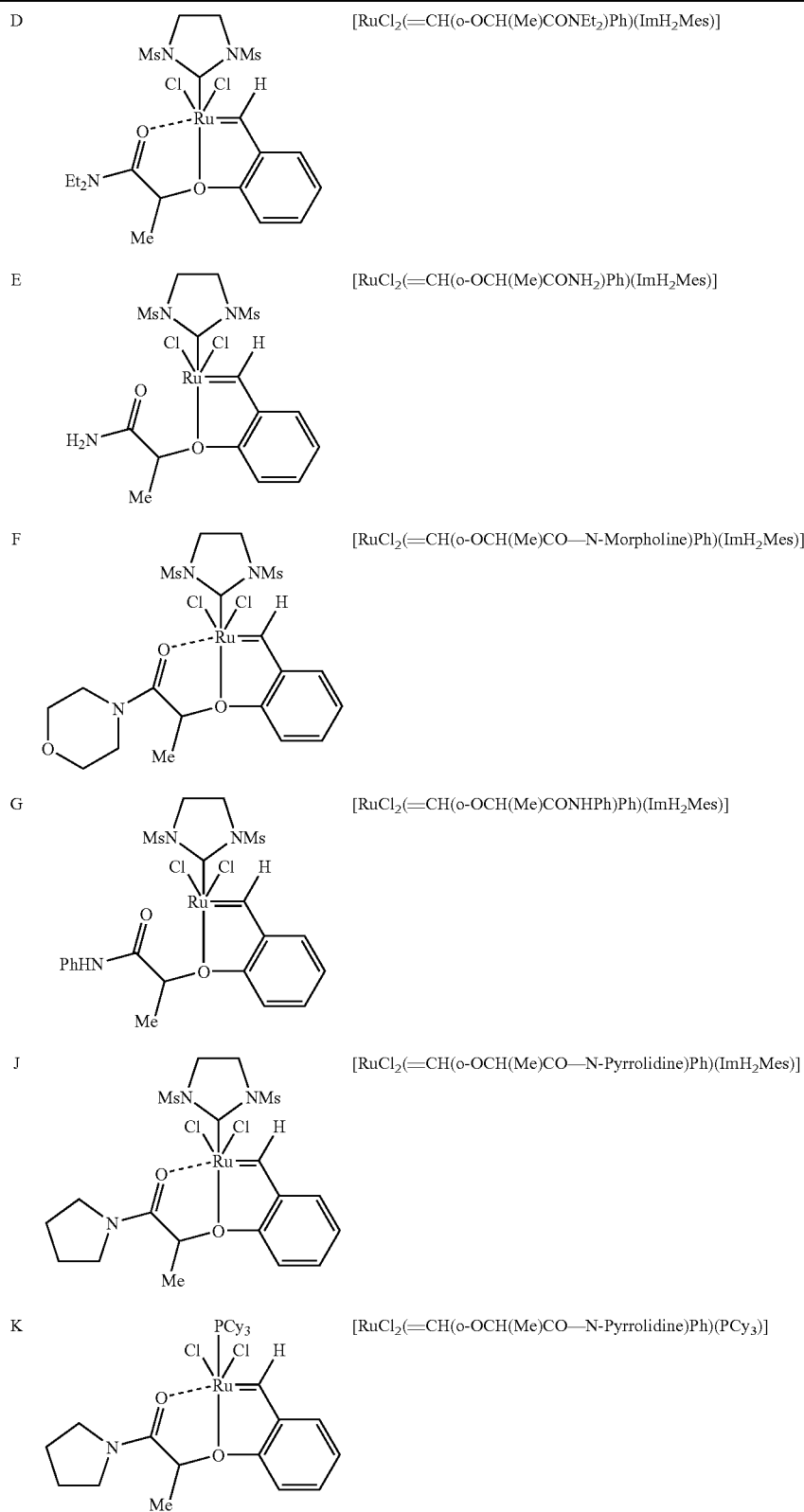

D [RuCl$_2$(=CH(o-OCH(Me)CONEt$_2$)Ph)(ImH$_2$Mes)]

E [RuCl$_2$(=CH(o-OCH(Me)CONH$_2$)Ph)(ImH$_2$Mes)]

F [RuCl$_2$(=CH(o-OCH(Me)CO—N-Morpholine)Ph)(ImH$_2$Mes)]

G [RuCl$_2$(=CH(o-OCH(Me)CONHPh)Ph)(ImH$_2$Mes)]

J [RuCl$_2$(=CH(o-OCH(Me)CO—N-Pyrrolidine)Ph)(ImH$_2$Mes)]

K [RuCl$_2$(=CH(o-OCH(Me)CO—N-Pyrrolidine)Ph)(PCy$_3$)]

-continued

L [RuCl$_2$(=CH(o-OCH(Me)CO—N-Pyrrolidine)Ph)(SIPrNap)]

M [RuCl$_2$(=CH(o-OCMe$_2$CO—N-Pyrrolidine)Ph)(ImH$_2$Mes)]

N [RuCl$_2$(=CH(o-OCH$_2$CO—N-Pyrrolidine)Ph)(ImH$_2$Mes)]

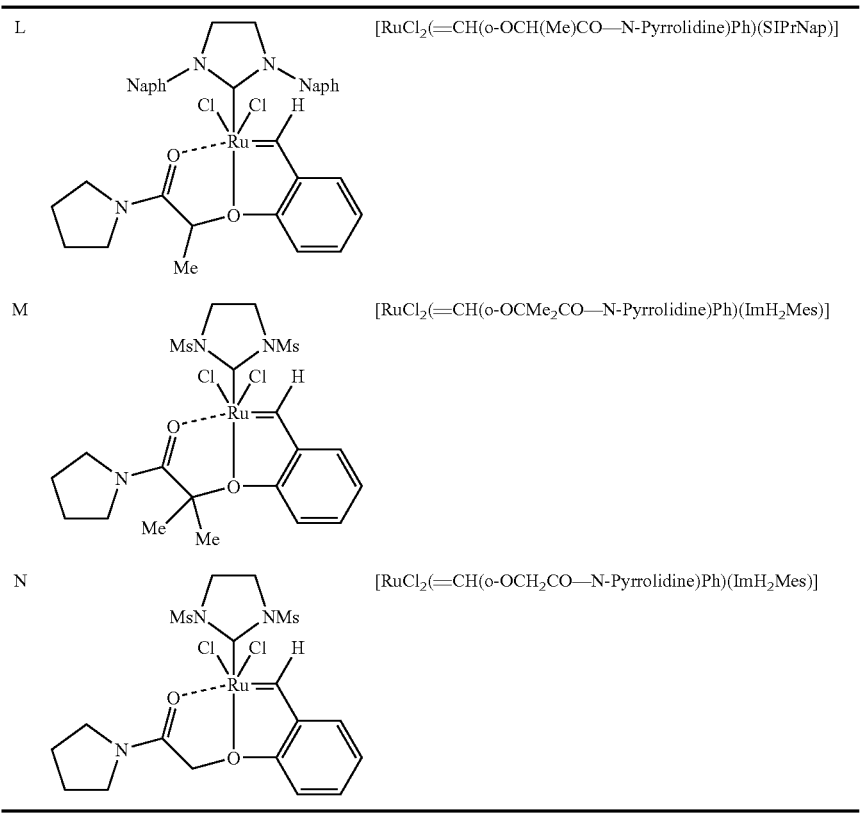

EXAMPLES

Abbreviations r.t.=room temperature

ImH$_2$Mes=1,3-bis-(2,4,6-trimethylphenyl)-2-imidazolidinylidene

RP column=reverse phase column

Cy=cyclohexyl

Mes=2,4,6-trimethylphenyl

Naph=2,7-di-isopropyl-naphth-1-yl

Example A1

2-[((E,Z)-2-Propenyl)-phenoxy]-propionic acid

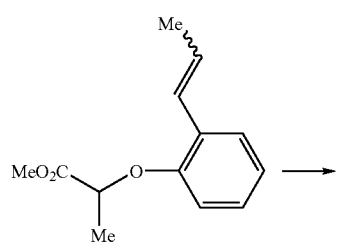

→

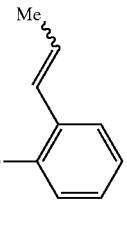

To a solution of 0.50 g (2.2 mmol) of methyl 2-[((E,Z)-2-propenyl)-phenoxy]-propanoate (4:1 mixture of E/Z-isomers, prepared according to D. Arlt, K. Grela et al, J. Am. Chem. Soc. 2006, 128:13652-13653) in dioxane, 11 mL (20.0 mmol) of a 2M aqueous sodium hydroxide solution was added and the reaction mixture was stirred for 16 h at rt. To the reaction mixture were added 50 mL of water and 100 mL of tert-butyl methyl ether. The organic layer was washed with 40 mL of water. After the pH of the combined aqueous layers was adjusted to pH ca. 1 with 25% aqueous hydrochloric acid, 150 mL of dichloromethane was added. The organic layer was washed with 100 mL of brine, dried (Na2SO4), and evaporated to dryness at 40° C./10 mbar to yield 0.50 g (99% yield) of the title compound as a 3:1 mixture of E/Z-isomers with >99.9% purity (GC-area %) as white crystals. (GC method as described in Example 7. Retention times: Methyl 2-[((Z)-2-propenyl)-phenoxy]-propanoate 12.2 min, methyl 2-[((E)-2-propenyl)-phenoxy]-propanoate 12.9 min, 2-[((Z)-2-propenyl)-phenoxy]-propionic acid 13.3 min, 2-[((E)-2-propenyl)-phenoxy]-propionic acid 14.0 min): MP 96° C. MS 206.0 (M$^+$).

Example A2

2-[((E,Z)-2-Propenyl)-phenoxy]-1-pyrrolidine-1-yl-propan-1-one

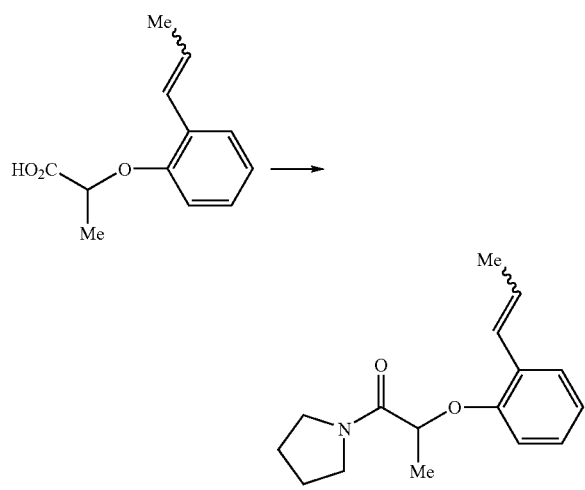

To a solution 1.92 mL (23.0 mmol) of pyrrolidine in 200 mL of N,N-dimethylformamide, 4.02 mL (23.0 mmol) of N,N-diisopropylethylamine, 1.00 g (4.6 mmol) of 2-[((E,Z)-2-propenyl)-phenoxy]-propionic acid (3:1 mixture of E/Z-isomers) and 1.92 g (5.8 mmol) of O-benzotriazol-1-yl-N,N,N',N'-tetramethyluronium tetrafluoroborate (TBTU) was added and the reaction mixture stirred for 2 h at rt. To the reaction mixture was added 200 mL of water and 400 mL ethyl acetate. The organic layer was separated, washed with 100 mL of water, dried ($Na_2SO_4$), and evaporated to dryness at 40° C./10 mbar. The crude title compound was purified by $SiO_2$ chromatography (heptane/ethyl acetate 3:1) to yield 0.69 g (57% yield) of the title compound as a 4:1 mixture of E/Z-isomers with 98.1% purity (GC-area %) as a white powder. (GC method: Column HP-5, 5% phenyl methyl siloxane, 30 m×0.32 mm, df: 0.25 µm; injector temp.: 250° C.; detector temp.: 250° C.; oven temp.: 50° C. to 300° (10° C./min), then 300° C. for 5 min; Retention times: 2-[((Z)-2-propenyl)-phenoxy]-propanoic acid 13.9 min, 2-[((E)-2-propenyl)-phenoxy]-propanoic acid 14.0 min, 2-[((Z)-2-propenyl)-phenoxy]-1-pyrrolidine-1-yl-propan-1-one 18.0 min, 2-[((E)-2-propenyl)-phenoxy]-1-pyrrolidine-1-yl-propan-1-one 18.4 min), MS: 260.0 (M+H$^+$).

Example B

1-Pyrrolidin-1-yl-2-(2-vinylphenoxy)-propan-1-one

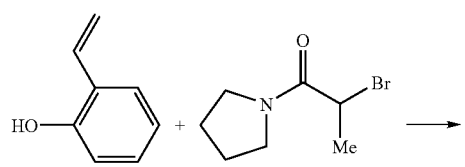

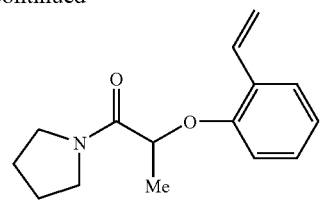

To a solution of 6.35 g (40.1 mmol) potassium 2-vinylphenolate in 110 mL of water (pH adjusted to 14 by addition of KOH) under argon was added 150 mL of toluene, 0.65 g (2.0 mmol) of tetrabutylammonium bromide and 11.54 g (50.16 mmol) of 2-bromo-1-pyrrolidin-1-yl-propan-1-one. The two-phase mixture was stirred vigorously over night at 45° C. After this time the organic phase was removed, washed with water, 4 M sodium hydroxide aqueous solution, 1 M hydrochloric acid solution and water, dried ($Na_2SO_4$), and evaporated to dryness. Crystallization of the residue from warm heptane (200 mL) afforded the title compound as a white powder (7.0 g, 70.5% yield): MP 85-86° C., MS: 246.1496 (M+H)$^+$, 268.1317 (M+Na)$^+$.

Example 1

Catalyst No. J, [RuCl$_2$(=CH(o-OCH(Me)CO—N-Pyrrolidine)Ph)(ImH$_2$Mes)]

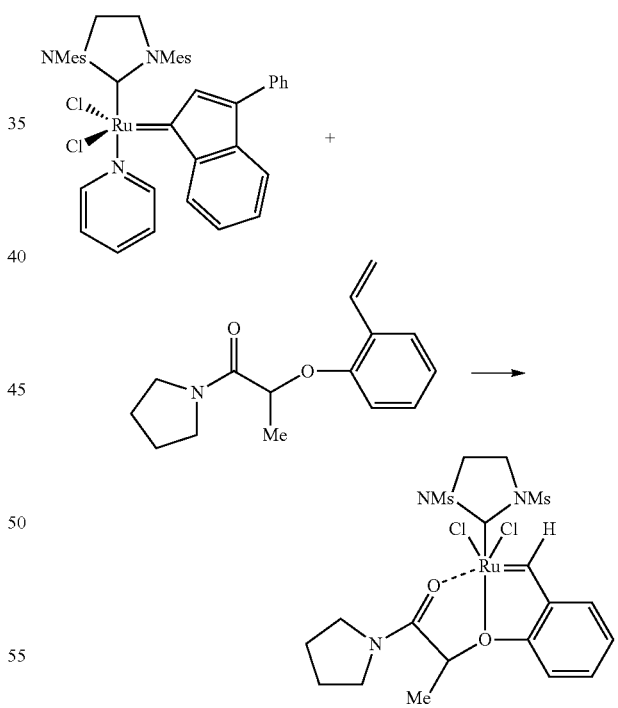

A mixture of 21.0 g (27.69 mmol) of [RuCl$_2$(3-phenylidenyl-1-iden)(ImH$_2$Mes)(pyridine)] and 7.48 g (30.46 mmol) of 1-pyrrolidin-1-yl-2-(2-vinylphenoxy)-propan-1-one in 230 mL of toluene was stirred for 2 h at 65° C. under argon. The reaction mixture (a suspension) was cooled with an ice bath, the precipitate was filtered off and washed with an ice-cold mixture of toluene, hexane and diethyl ether. The filter cake was dried at rt in vacuo for 20 h to afford 17.8 g of the title compound (90.6% yield) as a green powder.

Anal. calcd. for $C_{35}H_{43}Cl_2N_3O_2Ru$: C, 59.23; H, 6.11; N, 5.92; Cl, 9.99. Found: C, 59.63; H, 6.52; N, 5.70. Ru content: 14.03%. 1H-NMR ($CD_2Cl_2$): characteristic signal at 16.5 ppm (Ru=CH).

Example 2

Catalyst No. J, [RuCl$_2$(=CH(o-OCH(Me)CO—N-Pyrrolidine)Ph)(ImH$_2$Mes)]

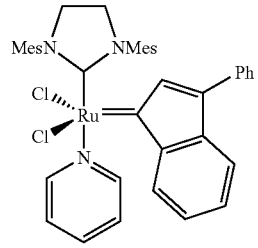

+

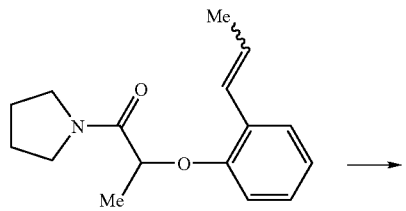

→

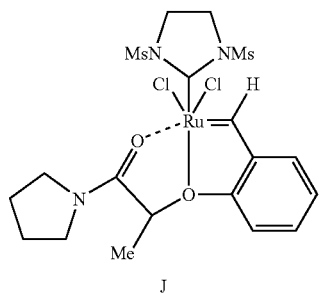

J

A mixture of 3.00 g (3.96 mmol) of [RuCl$_2$(3-phenylidenyl-1-iden)(ImH$_2$Mes)(pyridine)] and 1.16 g (4.35 mmol) of 2-[((E,Z)-2-propenyl)-phenoxy]-1-pyrrolidine-1-yl-propan-1-one in 50 mL of toluene was stirred for 4 h at 60° C. under argon. The reaction mixture (a suspension) was cooled with an icebath, the precipitate was filtered off and washed with an ice-cold mixture of toluene, pentane and diethylether. The filter cake was dried at room temperature in vacuo for 20 h to afford 2.38 g of the title compound (84.8% yield) as a green powder.

Anal. calcd. for $C_{35}H_{43}Cl_2N_3O_2Ru$: C, 59.23; H, 6.11; N, 5.92; Cl, 9.99. Found: C, 60.12; H, 6.06; N, 5.52. Ru content: 14.50%. 1H-NMR ($CD_2Cl_2$): characteristic signal at 16.5 ppm (Ru=CH).

We claim:
1. A process for the preparation of compounds of formula I

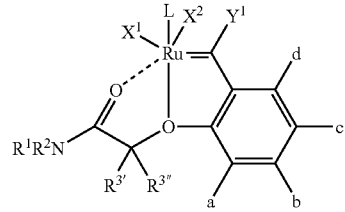

wherein:
the dotted line signifies an optional bond;
L is a neutral ligand;
$X^1$ and $X^2$ are independently anionic ligands;
$Y^1$ is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl or $C_{1-6}$-alkylsulfinyl;
a, b, c and d independently of each other have the meaning of hydrogen, $C_{1-6}$-alkyl, halogen-$C_{1-6}$-alkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl-or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$—$C_{1-6}$-alkyl or $OSi(C_{1-6}$-alkyl$)_3$ and $SO_2$—NR'R" wherein R' and R" are independently hydrogen, aryl or $C_{1-6}$-alkyl or R' and R" together with the N atom form a cyclic amine;
$R^1$ and $R^2$ are independently hydrogen, $C_{1-6}$-alkyl, $C_{3-8}$-cycloalkyl, aryl or aryl-$C_{1-6}$-alkyl; or,
$R^1$ and $R^2$ together with the N atom form a 5 to 8 membered cyclic amine which may contain nitrogen, oxygen or sulfur as additional hetero atom;
$R^{3'}$ and $R^{3''}$ are independently hydrogen, $C_{1-6}$-alkyl, $C_{3-8}$-cycloalkyl, aryl, aryl-$C_{1-6}$-alkyl,
comprising contacting a Ru complex of formula II

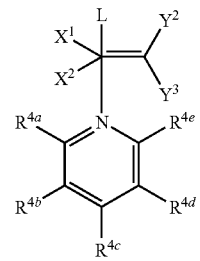

wherein:
$X^1$, $X^2$ and L are as defined above and
$Y^2$ and $Y^3$ independently of each other are hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl, or, $Y^2$ and $Y^3$ taken together form a carbene of the type

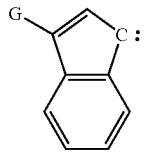

2a wherein G is hydrogen or aryl; or,
$Y^2$ and $Y^3$ together form a vinyl or cumulenyl carbene of formula 2b or 2c:

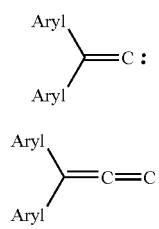

2b

2c wherein $R^{4a}$, $R^{4b}$, $R^{4c}$, $R^{4d}$, $R^{4e}$ independently of each other are hydrogen, $C_{1-6}$-alkyl, $C_{1-6}$-alkyloxy, aryl, aryloxy, halogen, $C_{1-6}$-alkylcarbonyl amino or arylcarbonyl amino;
with a compound of formula III

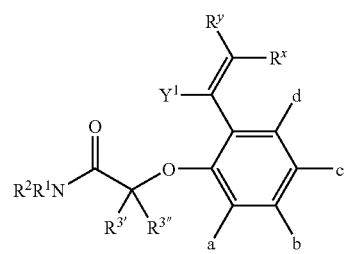

III wherein
$R^1$, $R^2$, $R^{3'}$, $R^{3''}$, $Y^1$ and a, b, c, d are as defined above;
$R^x$ and $R^y$ are independently hydrogen, $C_{1-6}$-alkyl optionally substituted by one or more halogen atoms, or, aryl optionally substituted by one or more halogen atoms or by $C_{1-6}$-alkyl.

2. A process according to claim 1 wherein L in the Ru complex of the formula II is 2q, 2r, 2s or 2t wherein:

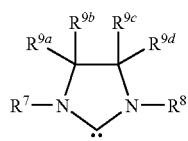

2q

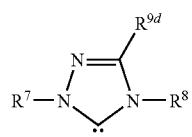

2r

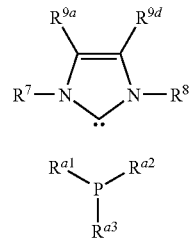

2s

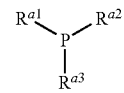

2t $R^7$ and $R^8$ are independently $C_{1-6}$-alkyl, aryl, $C_{2-6}$-alkenyl or 1-adamantyl and $R^{9a-d}$ are independently hydrogen, $C_{1-6}$-alkyl, $C_{2-6}$-alkenyl or aryl, or $R^{9b}$ and $R^{9c}$ or $R^{9a}$ and $R^{9d}$ taken together form a —$(CH_2)_4$-bridge; or, $R^{9a}$ and $R^{9d}$ in formula 2s both are halogen; and, $R^{a1}$, $R^{a2}$ and $R^{a3}$ are independently $C_{1-6}$-alkyl, $C_{3-8}$-cycloalkyl, aryl, heteroaryl or $R^{a1}$ and $R^{a2}$ or $R^{a2}$ and $R^{a3}$ or $R^{a1}$ and $R^{a3}$ taken together form a 1,5-bridged cyclooctyl group.

3. A process according to claim 1 wherein $Y^2$ and $Y^3$ in the Ru compound of the formula II are taken together to form a compound of formula 2a:

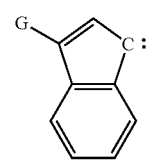

2a wherein G is hydrogen or aryl.

4. A process according to claim 1 wherein $X^1$ and $X^2$ in the Ru complex of formula II is a halogenide or a pseudo halogenide.

5. A process according to claim 1 wherein $R^{4a}$, $R^{4b}$, $R^{4c}$, $R^{4d}$ and $R^{4e}$ are hydrogen, methyl or halogen.

6. A process according to claim 1 wherein the compounds of formula III are selected from IIIa, IIIb, IIIc, IIId, IIIe, IIIf, IIIg or IIIh:

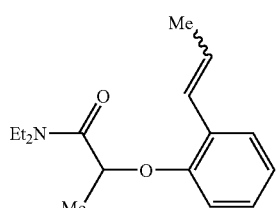

IIIa

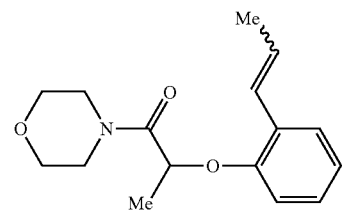

IIIb

IIIc

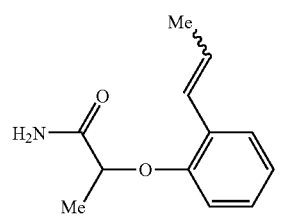

IIId

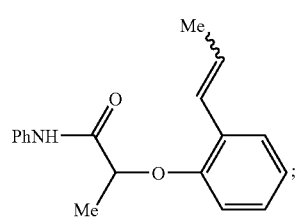

IIIe

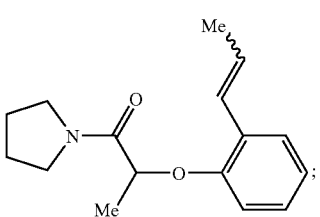

IIIf

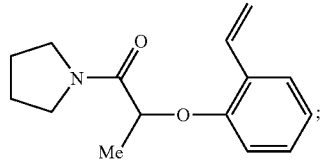

IIIg

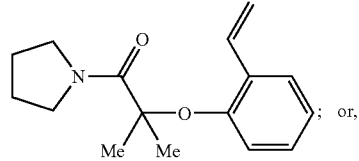

; or,

IIIh

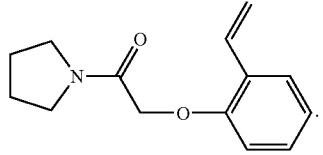

.

7. A process according to claim 1 wherein the conversion is performed in an inert organic solvent at a temperature of 0° C. to 100° C.

8. A process according to claim 7 wherein the inert organic solvent is an aromatic solvent, a halogenated aromatic solvent, a halogenated hydrocarbon or a mixture of said inert organic solvents with an aliphatic hydrocarbon.

9. A process according to claim 1 wherein the compound of formula I is selected from the group consisting of:

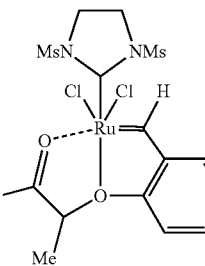

[RuCl$_2$(=CH(o-OCH(Me)CONEt$_2$)Ph)(ImH$_2$Mes)]

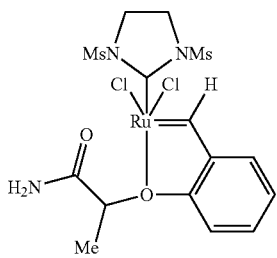

[RuCl$_2$(=CH(o-OCH(Me)CONH$_2$)Ph)(ImH$_2$Mes)]

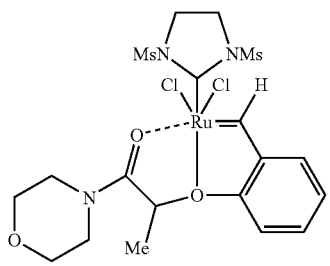

[RuCl$_2$(=CH(o-OCH(Me)CO—N-Morpholine)Ph)(ImH$_2$Mes)];

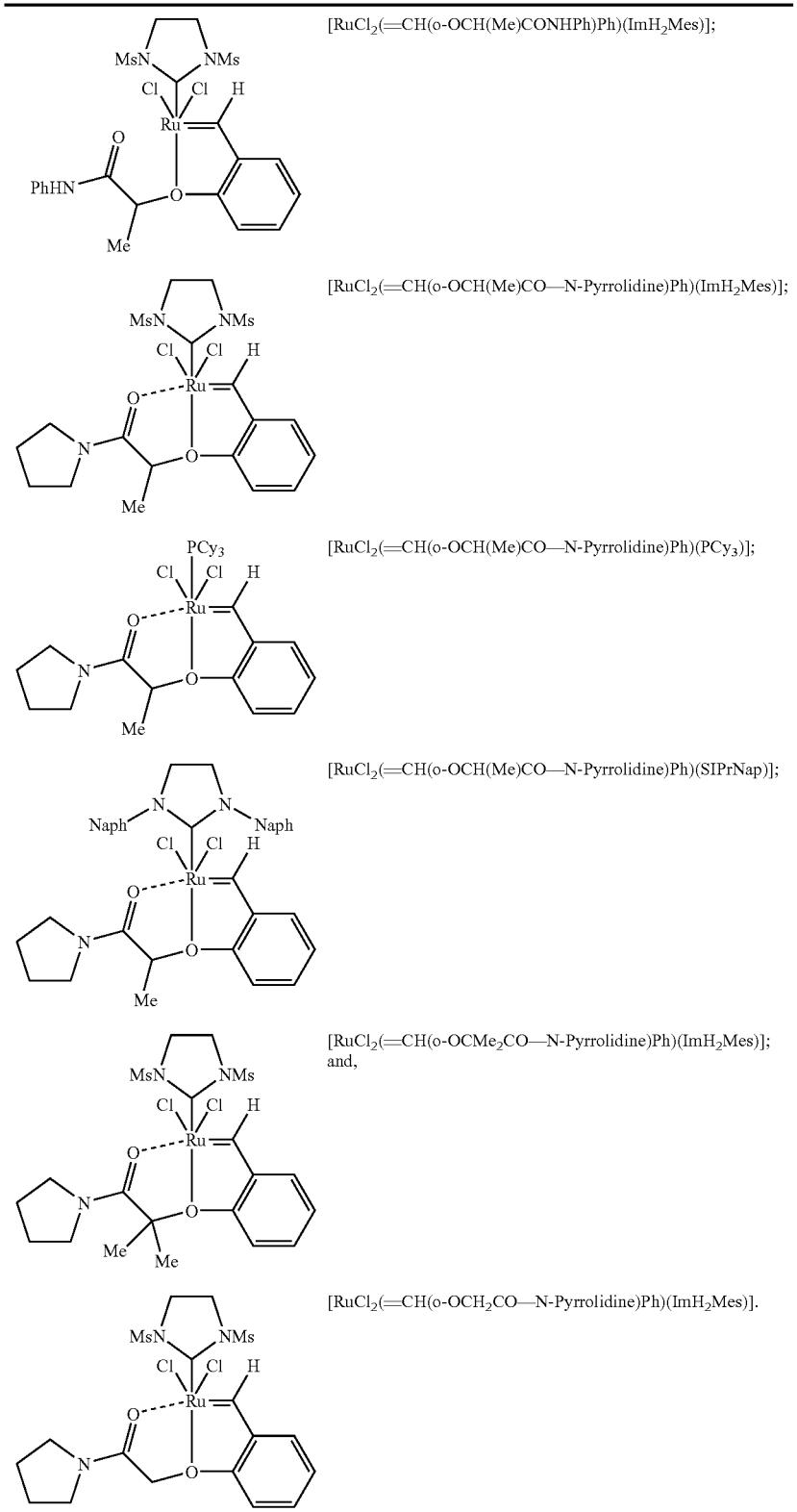
[RuCl$_2$(=CH(o-OCH(Me)CONHPh)Ph)(ImH$_2$Mes)];
[RuCl$_2$(=CH(o-OCH(Me)CO—N-Pyrrolidine)Ph)(ImH$_2$Mes)];
[RuCl$_2$(=CH(o-OCH(Me)CO—N-Pyrrolidine)Ph)(PCy$_3$)];
[RuCl$_2$(=CH(o-OCH(Me)CO—N-Pyrrolidine)Ph)(SIPrNap)];
[RuCl$_2$(=CH(o-OCMe$_2$CO—N-Pyrrolidine)Ph)(ImH$_2$Mes)]; and,
[RuCl$_2$(=CH(o-OCH$_2$CO—N-Pyrrolidine)Ph)(ImH$_2$Mes)].
\* \* \* \* \*